(12) United States Patent
Hoffman et al.

(10) Patent No.: US 7,229,627 B2
(45) Date of Patent: Jun. 12, 2007

(54) APPARATUSES AND METHODS FOR THE PRODUCTION OF HAEMATOPHAGOUS ORGANISMS AND PARASITES SUITABLE FOR VACCINE PRODUCTION

(75) Inventors: Stephen L. Hoffman, Gaithersburg, MD (US); Thomas C. Luke, Brookville, MD (US)

(73) Assignee: Sanaria, Inc., Rockville, MD (US)

( * ) Notice: Subject to any disclaimer, the term of this patent is extended or adjusted under 35 U.S.C. 154(b) by 41 days.

(21) Appl. No.: 10/958,163

(22) Filed: Oct. 4, 2004

(65) Prior Publication Data

US 2005/0100532 A1 May 12, 2005

Related U.S. Application Data

(63) Continuation-in-part of application No. PCT/US03/10797, filed on Apr. 7, 2003.

(60) Provisional application No. 60/370,581, filed on Apr. 5, 2002.

(51) Int. Cl.
*A61K 39/15* (2006.01)

(52) U.S. Cl. ................................. 424/272.1

(58) Field of Classification Search ............. None
See application file for complete search history.

(56) References Cited

U.S. PATENT DOCUMENTS

| 4,850,305 | A | 7/1989 | Georgi |
| RE35,348 | E | 10/1996 | Georgi |
| 5,983,557 | A | 11/1999 | Perich |

OTHER PUBLICATIONS

Hurtado et al. "Regular production of infective sporozoites of Plasmodium falciparum and P. vivax in laboratory-bred Anopheles albimanus," Anals Trop. Med. & Parasit., 1997, 91, 49-60.*

Munderloh et al. "Anopheles stephensi and Toxorhynchites amboinensis: aseptic rearing of mosquito larvae on cultured cells," J. Parasit., 1982, 68, 1085-91, Abstract only.*

Tsuji et al. "Progress toward a Malaria Vaccine: Efficient Induction of Protective Anti-Malaria Immunity," Biol. Chem., 2001, 382, 553-70.*

Food and Drug Administration, "Guidance for Industry, Content and Format of Chemistry, Manufacturing and Controls Information and Establishment Description Information for a Vaccine or Related Product," 1999, http://www.fda.gov/cber/guidelines.htm.*

Rieckmann, KH et al, Sporozoite Induced Immunity in Man; Trans. Royal soc. Trop. Med. (1974) 68:258-259.

Clyde, DF et al. Specificity of Protection of Man Immunized Against Sporozoite-Induced Falciparum Malaria; Am. J. Med. Sci. (1973) 266:398-401.

Nussenzweig, RS et al, Protective Immunity Produced by the Injection of X-Irratiated Sporozoites of Plasmodium berghei; Nature (1967) 216: 160-162.

Clyde, DF et al, Immunization of Man Against Sporozoite-Induced Falciparum Malaria; Am. J. Med. Sci. (1973) 266:169-177.

Hoffmann, SL et al, Protection of Humans Against Malaria by Immunization; J. Infect. Dis. (2002) 185:1155-1164.

* cited by examiner

*Primary Examiner*—Cecilia J. Tsang
*Assistant Examiner*—Christina M. Bradley
(74) *Attorney, Agent, or Firm*—David Dolberg

(57) ABSTRACT

Disclosed are apparatuses and methods for the production of attenuated aseptic parasites in hematophagous insects generally, and production of *Plasmodium* species sporozoites in *Anopheles* species mosquitoes specifically; apparatuses and methods for the production of strains of hematophagous insects with desired properties such as hypoallergenicity or hyperinfectivity; methods of producing a parasite strain that is capable of withstanding cyropreservation at temperatures close to freezing; apparatuses and methods for the injection of an attenuated parasite vaccine; production of parasites and hematophagous insects that are free from contamination by unwanted biological agents; apparatuses for the reconstruction of complex parasitic life cycles aseptically to avoid the contamination of the parasite or the insect vector host with unwanted biological agents.

5 Claims, 11 Drawing Sheets

APPARATUSES AND METHODS FOR THE PRODUCTION OF HAEMATOPHAGOUS ORGANISMS AND PARASITES SUITABLE FOR VACCINE PRODUCTION

CLAIM OF PRIORITY

This application is a continuation in part of PCT/US03/10797, which has an International filing date of Apr. 7, 2003 and was published in English on Oct. 23, 2003 (WO 03/087322). This application further claims the benefit under 35 U.S.C.§119(e) of U.S. Provisional Application No. 60/370,581, filed Apr. 5, 2002. New material is filed under the provisions of 37 CFR §1.53(b) (2).

FIELD OF THE INVENTION

The present invention relates to apparatuses and methods for the production of parasites in hematophagous insects generally, and to the production of *Plasmodium* species sporozoites in *Anopheles* species mosquitoes, specifically. The present invention further relates to apparatuses a nd methods for the production of strains of insects (e.g., *Anopheles* mosquitoes) that have desired properties such as hypoallergenicity or hyperinfectivity. The present invention also relates to methods of producing a strain of a parasite that is capable of withstanding cyropreservation at temperatures close to freezing. The present invention further relates to apparatuses and methods for the injection of an attenuated parasite vaccine. The present invention allows for the production of parasites and hematophagous insects that are free from contamination by unwanted biological agents such as bacteria and other microorganisms. The apparatuses of the present invention provide for the reconstruction of complex parasitic life cycles aseptically, so as to avoid the contamination of either the parasite or the insect vector host with unwanted bio logical agents. The present invention also provides for methods for the production of an attenuated *Plasmodium* sporozoite vaccine that is stable at relatively shallow cryogenic temperatures. The present invention further provides for apparatuses for the delivery of micro-bolus amounts of vaccine.

DESCRIPTION OF THE BACKGROUND

Malaria is the most devastating parasitic disease and, as such, represents one of the most important public health problems worldwide. According to experts in the field, malaria infects 300 million people a year and kills up to 3 million people per year. A vaccine for malaria would drastically reduce the impact of this dangerous disease.

The causative agents in malaria are various species of the eukaryotic genus *Plasmodium*, including *Plasmodium falciparum, Plasmodium vivax, Piasmodium ovale*, and *Plasmodium Malariae*. These parasites have a very complex life cycle that involves both vertebrate and invertebrate hosts. The vertebrate infective form of the parasite (sporozoites) is present in the salivary glands of mosquitoes (typically of the genus *Anopheles*) and the sporozoites are transferred to humans during feeding by the mosquitoes. In the human host, the sporozoites initially infect the cells of the liver and eventually red blood cells. This infection results in an illness which is potentially fatal to those infected.

Current prophylactic approaches to malaria include the use of drugs, including chloroquine, mefloquine and atovaquone/proquanil. However, multiple drug resistant strains of *Plasmodium* have recently been observed. In addition, the occurrence of drug resistant strains of malaria is thought to be promoted by the use of these prophylactic antimalarial drugs. Accordingly, significant efforts have been undertaken to develop a vaccine for malaria.

There have been some indications in the scientific literature that a vaccine for malaria could be effective. In regards to a metabolically active non-replicating (attenuated) whole sporozoite vaccine, Nussenzweig and coworkers (Nature 216: 160-162; 1967) reported that immunizing mice with radiation attenuated *Plasmodium berghei* sporozoites. These rodent studies provided the impetus for human studies, and during the 1970s, Cylde, Rieckmann, and colleagues (Clyde et al.; Am. LT. Med. Sci. 266:169-177; 1973; Clyde et al. Am. LT. Med. Sci. 266:398-401; 1973; Rieckmann et al. Trans. R. Soc. Trop. Med. Hyg. 68:258-259; 1974) conducted limited studies that established that immunizing human volunteers with the bites of irradiated mosquitoes carrying *Plasmodium falciparum* sporozoites in their salivary glands could protect volunteers against a challenge with fully infectious *Plasmodium falciparum* sporozoites. Hoffman and Luke (Hoffman et al.; LT. Infect. Dis. 185: 1155-1164; 2002) established the full potential of this approach by reporting the results of 10 years' clinical experience with live mosquito immunizations and challenges, and combined their results with all the published clinical reports of immunizing humans with irradiated *Plasmodium* sporozoites.

The following 3 points summarize the most importaht findings: 1) Thirteen of 14 volunteers immunized by the bites of greater than 1000 infected, irradiated mosquitoes were protected against developing blood-stage *P. falciparum* infection when challenged within 10 weeks of their last primary immunization; 2) Five of 6 of the 14 volunteers in (1) above when challenged from 23 to 42 weeks (23, 36, 39, 41, and 42 weeks) after their last primary or secondary immunization were protected against experimental challenge; and 3) Seven of seven heterologous challenges (immunized with one strain of *P. falciparum* and challenged with another strain of *P. falciparum*) in four individuals were associated with complete protection.

From this, it was demonstrated that protection was achieved in greater than 90% of immunized subjects, lasted for at least 10 months, and demonstrated cross strain (heterologous) protection. For the first time, the true efficacy of this experimental vaccine approach was demonstrated. While this study demonstrated the feasibility of an attenuated malaria vaccine, it was considered for many reasons to be impractical to immunize large numbers of susceptible individuals by employing the bites of irradiated infected mosquitoes.

One technical hurdle to the development of a clinically relevant vaccine is the production of aseptic sporozoites that are free of contamination by unwanted biological agents. Currently, it is not possible to produce *Plasmodium falciparum* sporozoites using an in vitro process. Therefore, *Plasmodium falciparum* sporozoites must be obtained from the tissues of infected female *Anopheles* mosquitoes. However, it is well known that wild and insectary reared mosquitoes are highly contaminated with unwanted biological agents including bacteria, molds, and fungi. This contamination largely prevents the use of mosquito derived parasites in a clinically relevant vaccine suitable fore regulatory licensure. An apparatus and method to produce aseptic *Anopheles* mosquitoes for the in vivo production of *Plasmodium falciparum* sporozoites is a critical step in the development of an acceptable attenuated sporozoites vaccine from both a clinical and regulatory perspective.

Contamination of mosquitoes with unwanted biological agents may arise from several sources in the mosquito's life cycle. The surface of mosquito eggs may become contaminated during oviposition from the female mosquito's genital tract and ovipositors. The larvae may retain microbes in their gastrointestinal tract and peritrophic membrane during metamorphosis of larvae to pupae and adult mosquitoes. In addition, multiple environmental factors, including the aquatic habitat of the larvae, the external environment of the adult mosquito, and contaminated skin of an animal upon which the mosquito fed, may contribute to contamination of mosquitoes and thus the *Plasmodium* parasite.

For decades, non-aseptic sporozoites have been routinely obtained from infected *Anopheles* mosquitoes for research purposes using labor intensive techniques. There are multiple drawbacks to this standard approach. Since the entire process is conducted under non-sterile conditions, the sporozoites preparation is usually contaminated with microbes. Though sporozoites can be partially purified by a variety of techniques, contamination of the resulting product makes it unsuitable for use in developing a vaccine for human use. Microbially contaminated vaccines can cause an iatrogenic infection of a serious nature in both humans and animals. In addition, the processes of the prior art for rearing non-aseptic mosquitoes are labor intensive and require multiple direct manipulations of the mosquitoes during their life cycle.

Accordingly, one of the limitations in the production of a vaccine for malaria is the ability to obtain a large number of aseptic sporozoites of *Plasmodium* species. As stated above, sporozoites that are obtained from *Anopheles* species of mosquitoes using standard techniques results in sporozoites that are not useful in the development of an attenuated sporozoite vaccine. Aseptic sporozoites could be used as a vaccine to generate protective immunological responses safely and efficiently. In addition, the production of such aseptic sporozoites will be a regulatory requirement for the commercial production of a malaria vaccine.

Thus, there has been a long standing need in the medical field for the production of aseptic *Plasmodium* species. sporozoites and aseptic *Anopheles* mosquitoes for use in the development of a vaccine for malaria. Apparatuses and methods for the aseptic rearing of *Anopheles* mosquitoes and *Plasmodium* parasites can also be used for the aseptic production of other hematophagous insect species and parasites for other critically needed vaccines against parasitic diseases of humans and animals.

In order to develop strains of insects that possess certain desired properties (e.g., hyperinfectivity or hypoallergenicity), it would be useful to employ a device that would allow experiments selectively to evaluate the biting behavior and properties of individual insects. The apparatus would also be useful in the selection of insects that possessed desired properties.

An additional hurdle for the efficient and economical development of an attenuated vaccine for malaria is the deleterious effect that the *Plasmodium* parasite has on the mosquito host. *Anopheles* mosquitoes are capable of transmitting *Plasmodium* sporozoites to a host animal on which they feed. Research indicates that *Plasmodium* infections of *Anopheles* female mosquitoes are deleterious to the survival of mosquitoes in both the laboratory and wild-type environment. Thus, the ability to extract large numbers of mosquito phase parasites from female mosquitoes is currently limited by the inability of the mosquitoes to tolerate a heavy *Plasmodium* parasite burden.

A unique strain of *Anopheles* mosquito that is tolerant to massive infection with the *Plasmodium* parasite sporozoites from mosquitoes more efficient. The development of an attenuated *Plasmodium* sporozoites vaccine derived from this unique strain of *Anopheles* mosquitoes would thereby be more efficient and economical.

An additional possible difficulty in producing live, attenuated, or killed pathogen vaccines extracted from mosquito tissue is the potential of mosquito antigens to cause hypersensitivity, Arthus, or delayed type hypersensitivity reactions in the inoculated human or animal. Many hypersensitivity salivary antigens in several mosquito species have been identified. These salivary antigens probably confer a survival advantage to wild-type mosquitoes for numerous reasons. However, in laboratory maintained mosquito populations, such antigens are vestiges of their wild ancestors and are probably no longer necessary for selective survival advantage. By developing a technique to create hypoallergenic mosquitoes, it would be possible to create several hypoallergenic mosquito species (*Anopheles, Aedes, Culex*, etc.) which are specific to a wide variety of mosquito borne infections. These hypoallergenic strains of mosquitoes would have significant utility in the production of safe and effective attenuated parasite vaccines.

Once an attenuated vaccine has been developed, the vaccine should be delivered to an individual in need effectively. However, the standard manner in which vaccines are delivered—bolus injection via a syringe—is not effective in the case of an attenuated malarial vaccine. Vaccines syringes are commonly available in a variety of sizes with an industry standard locking port to which needles of various gauges can be attached. Usually, this system is adequate for typical vaccines, as the required volume is in the range of 500 to 1000 micro liters. Small volume variations from immunization to immunization have no effect on the immunogenicity of the typical vaccine.

However, in some vaccines, such as an attenuated *Plasmodium* sporozoite vaccine, the inoculum may be to be on the order of a micro liter or less—similar to the injectate of a probing mosquito. Larger volumes may cause the carrying liquid of the vaccine to disturb tissue integrity and cause the liquid to follow tissue planes. In mice, virtually all sporozoite challenge studies and attenuated sporozoites immunization studies are accomplished by intravenous injection of sporozoites, because non-intravenous administration of sporozoites in skin, subcutaneous tissue, and muscle has been associated with much lower infection rates and protection rates. When injected into the skin, sporozoites likely expire within the spaces between tissue planes created by the fluid in which the sporozoites are suspended, providing no opportunity to move throughout the host's cellular structures and into a capillary.

The standard procedure for current vaccines is therefore unsuitable for an ultra-low volume vaccine. To overcome this limitation, one could design a single use micro needle and syringe assembly. While this approach would likely be effective, it would also be impractical as millions of vaccines are to be given in extremely poor countries. Preferably, a malarial vaccine delivery system would be able to both deliver ultra-low volume boluses and also employ standard syringe assemblies as a cost saving measure.

Hurdles also exist for the delivery of frozen attenuated *Plasmodium* vaccine to individuals survive freezing temperatures in various preservation solutions. The best results, measured after re-warming and estimating the percentage of motile sporozoites and the ability to cause a patent blood stage infection after injection into a study animal, demonstrate that extremely low temperatures (−196 to −70 degrees Celsius) can preserve the sporozoites for many years. However, as preservation temperatures approach zero degrees Celsius, the percentage of viable sporozoites as a function of time drops precipitously in a temperature dependent fashion. This drop in viability limits the utility of malaria vaccines derived from attenuated sporozoites that must retain a high degree of potency during storage and shipment.

The worldwide cold storage and shipment infrastructure is robust and almost all countries have the capability to store relatively large volumes of materials at temperatures approaching zero degrees Celsius. At close to zero degrees Celsius, existing equipment and infrastructure can be adopted to transport an attenuated sporozoite vaccine to even the most remote locations on Earth. A storage and shipment infrastructure that requires temperatures in the range of minus seventy degrees Celsius, though technically feasible, is likely to be routinely possible in only the more technologically advanced nations. However, such extreme cold temperatures require special equipment, care, and will probably entail a large capital expenditure to accommodate the logistics of delivering an attenuated sporozoite vaccine.

The cyropreservation studies of sporozoites have used *Plasmodium* strains and clones developed for purposes other than developing a freeze tolerant strain of *Plasmodium* sporozoites. All organisms, to some degree, have the capability to survive temperature variations by utilizing stabilizing proteins, heat shock proteins, sugars, and carbohydrates which prevent the denaturing of critical enzymes, proteins, or limit the damage to cellular substrates caused by ice crystal formation. The malaria parasite, whose life cycle includes passage through the *Anopheles* mosquito, must have the ability to withstand natural variations in temperature—sometimes quite side as many temperate/tropical climates can vary by thirty to fifty degrees Fahrenheit in a day-night cycle. It can be assumed that genetic variation from *Plasmodium* organism to organism in nature has led to a wide variation in the ability of sporozoite to withstand temperature extremes.

The key to developing a *Plasmodium* species better able to survive high temperature cyropreservation conditions is to breed selectively those sporozoites shown to have that capacity. By selecting those sporozoites that survive increasingly high cyropreservation temperatures for longer periods of time while still able to complete a natural life cycle, one can develop a *Plasmodium* strain that has much greater utility in an attenuated whole-parasite vaccine for worldwide use.

SUMMARY OF THE INVENTION

In accordance with the present invention, there are provided systems and methods for the aseptic production of hematophagous insect vectors and parasites, generally, and production of *Anopheles* species mosquitoes and *Plasmodium* species sporozoites, specifically.

The present invention preferably allows for the aseptic production of parasites through the use of a sterile environment that is capable of supporting all stages of the parasite-insect life cycle. Insects are preferably grown from surface-sterilized eggs and the growing insects are provided with filtered air, sterile water, and sterile developmental-stage appropriate nutrition during metamorphosis from egg to adult. After reaching maturity, the insects are provided with a sterile, infectious blood meal that contains the infectious form of the parasite that is to be produced.

The present invention also provides for stunning the infectious insects, allowing for efficient collection of the immobile infected insects in a safe fashion, which may then be processed for collection of parasites.

The present invention may be used to produce a wide variety of aseptic parasites of vertebrate animals that have an obligate propagative, cyclo-development or cyclo-propagative life cycle phase in a hematophagous insect. Examples of suitable parasites and hematophagous insect and parasite pairs include, but are not limited to *Plasmodium falciparum-Anopheles stephensi*, *Trypanosoma cruzi-Triatoma infestans*, and *Aedes quadrimaculatus-Wuchereria bancrofti*.

It is thus an object of the present invention to produce aseptic parasites of vertebrate Animals sterilely, safely, and economically for research purposes. The aseptic parasites produced by the apparatuses and methods of the present invention are preferably suitable for development of human and animal vaccines. The present invention relates to apparatuses and methods for the production of parasites in hematophagous insects generally, and to the production of *Plasmodium* species sporozoites in *Anopheles* species mosquitoes, specifically. The present invention further relates to apparatuses and methods for the production of strains of Insects (e.g., *Anopheles* mosquitoes) that have desired properties such as hypoallergenicity or hyperinfectivity. The present invention also relates to methods of producing a strain of a parasite that is capable of withstanding cyropreservation at temperatures close to freezing. The present invention further relates to apparatuses and methods for the injection of an attenuated parasite vaccine. The present invention allows for the production of parasites and hematophagous insects that are free from contamination by unwanted biological agents such as bacteria and other microorganisms. The apparatuses of the present invention provide for the reconstruction of complex parasitic life cycles aseptically, so as to avoid the contamination of either the parasite or the insect vector host with unwanted biological agents. The present invention also provides for methods for the production of an attenuated *Plasmodium* sporozoite vaccine that is stable at relatively shallow cryogenic temperatures. The present invention further provides for apparatuses for the delivery of micro-bolus amounts of vaccine.

DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

Figure 1:
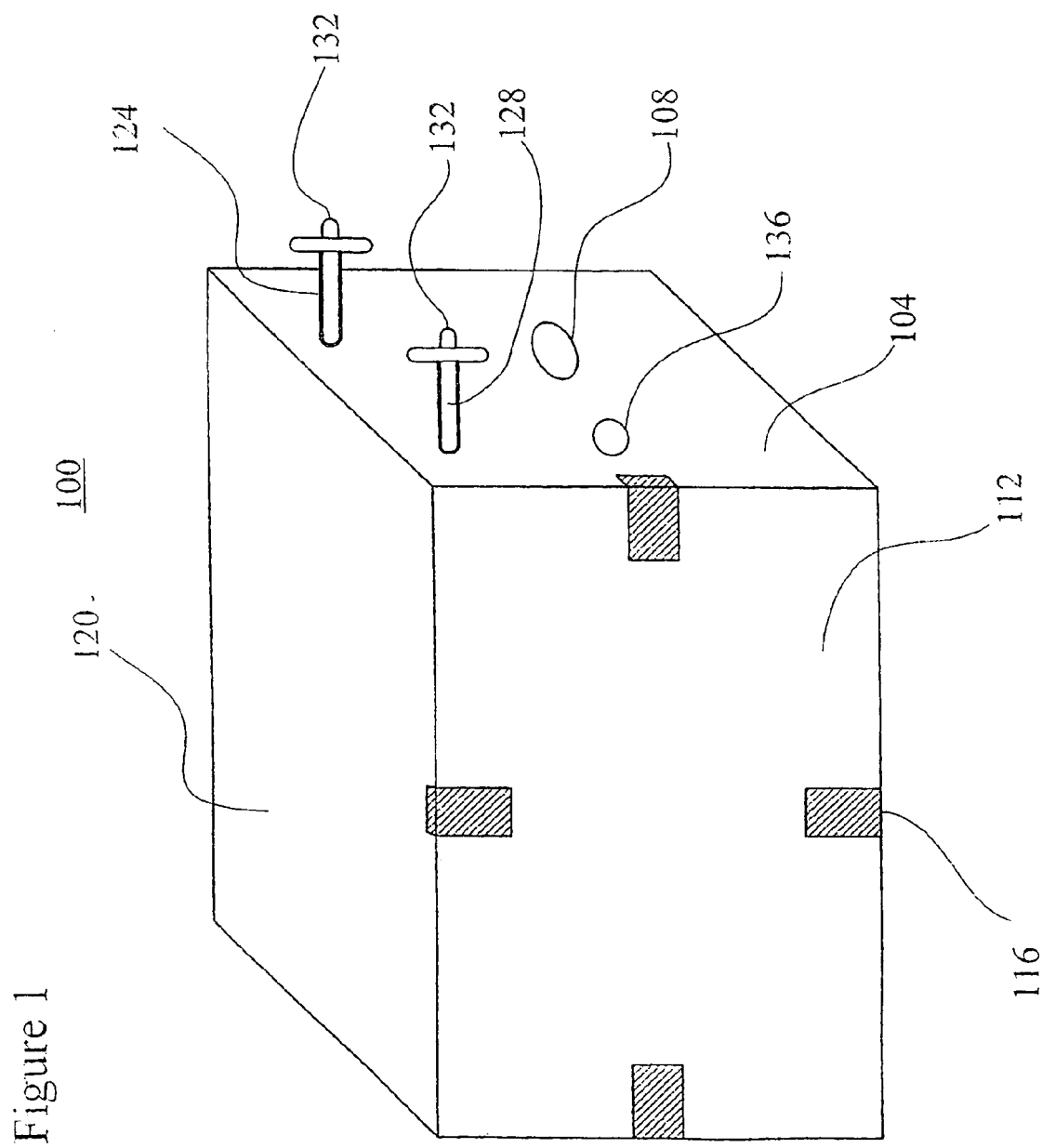
FIG. 1 is an external view of a presently-preferred embodiment of a parasite production chamber.

It is to be understood that the figures and descriptions of the present invention have been simplified to illustrate elements that are relevant for a clear understanding of the invention. The detailed description will be provided herein below with reference to the attached drawings.

Generally, the present invention provides apparatuses and methods for the production of parasites in hematophagous insects. The present invention preferably supports this production at multiple steps—from selection of species of insects and parasites with certain desired properties, to growth of aseptic parasites for use in the development of an attenuated vaccine, to the delivery systems for the injection of the attenuated vaccine. The various aspects and embodiments of the present invention may be utilized together or as individual components in the production and delivery of an attenuated vaccine. While the various aspects and embodiments of the present invention may be described with specific reference to the production of *Plasmodium* species sporozoites, it will be appreciated by those of skill in the art that the teachings herein are applicable to other insect stage infectious parasites. In addition, the descriptions found herein may make specific reference to *Anopheles* mosquitoes, but one of skill in the art will recognize that the teachings found herein are applicable to other hematophagous insects.

One aspect of the present invention provides apparatuses and methods for the production of insect stage parasites of vertebrate animals in hematophagous insects produced under aseptic conditions in vivo. These aseptic parasites and hematophagous insects are contemplated to be useful in the production of protective vaccines and in experimental research. While the aseptic production of numerous parasite-hematophagous insect pairs is contemplated as being within the scope of the present invention, the *Plasmodium* species parasite and the *Anopheles* mosquito will be used as an illustrative example.

The present invention preferably provides for a parasite production chamber that is designed to prevent microbial contamination of the internal environment where the hematophagous insects and parasites are being grown. This allows the parasite production chamber to be located in a non-sterile external environment during insect and parasite maturation such as a heated room with diurnal light. Operators are not required to wear protective clothing, masks, gloves, or shoe covers, which significantly improves comfort, efficiency, and operating expense. Additionally, the parasite production chambers of the present invention preferably physically separate infectious *Anopheles* mosquitoes from the operator preventing an accidental bite that could cause a potentially dangerous malaria infection.

The preferred embodiments of the present invention provide for the aseptic production of hematophagous insects and parasites through establishing a sterile environment in which the insects and parasites are grown. The sterility of this environment is preferably maintained for the duration of the insect parasite pair life cycle. The chambers and internal components of the parasite production chambers of the present invention are preferably sterile at the beginning of the growth procedure. Surface sterilized insect eggs are preferably employed when initially growing the insect colony. In addition, the blood on which the adult hematophagous insects feed, and which preferably provides the parasite to the insects, is also free from microbial contamination. In addition, the water, larva growth broth, feeding solutions, and all other solutions and materials used in the parasite production chambers of the present invention are also preferably sterile. Any standard means for sterilization may be employed including, but not limited to, autoclaving, chemical sterilization, irradiation, and micro-filtration. Additional sterilization techniques will be well known to one of skill in the art.

In a presently-preferred embodiment of the present invention, the parasite production chamber is constructed from high temperature-resistant materials such as metal, glass, or plastic compounds. The general shape may be rectangular or a cube of variable dimensions. The interior of a presently-preferred parasite production chamber of the present invention houses various components that support the parasite insect host stage life cycle requirements and can be physically divided into sections as is dictated by the parasite-insect host couple to be produced.

The various inlet and outlet tubes, mechanical ports, and reservoirs of parasite production chamber of the present invention will be described, followed by a description of the methods and operation of the apparatus of the present invention.

A front view of a presently-preferred embodiment of the present invention 100 is displayed in FIG. 1. Three side walls 104 are made with a provision for glass or clear plastic view ports 108 with airtight seals. The final side 112 is preferably outfitted with a hatch allowing access to the interior of the chamber for cleaning and parasite production preparation. The inner rim of the hatch preferably has a continuous rubber gasket to provide for an airtight seal to the sidewall of the apparatus. Compression latches 116 arranged on the periphery of the hatch allow for the rubber gasket to be squeezed tightly against the sidewall. Non-volatile, non-toxic lubricants such as glycerol can be coated on the rubber gasket to improve the airtight seal of the hatch when the previously mentioned hatches are engaged. The top of the parasite production chamber 120 is preferably a clear material such as glass or Plexiglas that can be reinforced on its inner side by a metal lattice. The clear top allows for viewing of the inner chamber and allows light to penetrate for diurnal variation of light, which may be necessary for the development of many insects.

A plurality of metal tubes 124 128 extend from the interior to the exterior of the parasite production chamber. Where the tube passes through the wall of the parasite production chamber, a metal or epoxy weld secures the tube and creates an airtight seal. The tubes allow for the sterile transfer of gasses and liquids into and out of the apparatus. The liquids may be introduced either into reservoirs or into feed apparatuses as described herein below. Each tube has a different purpose depending upon the parasite species and insect species being produced. In addition, each tube preferably has a micro-pore filter 132 attached to its exterior end to prevent contamination of the interior of the parasite production chamber. The parasite production chamber of the present invention also preferably includes operable access ports 136 that allow physical access to the interior of the parasite production chamber.

Figure 2:
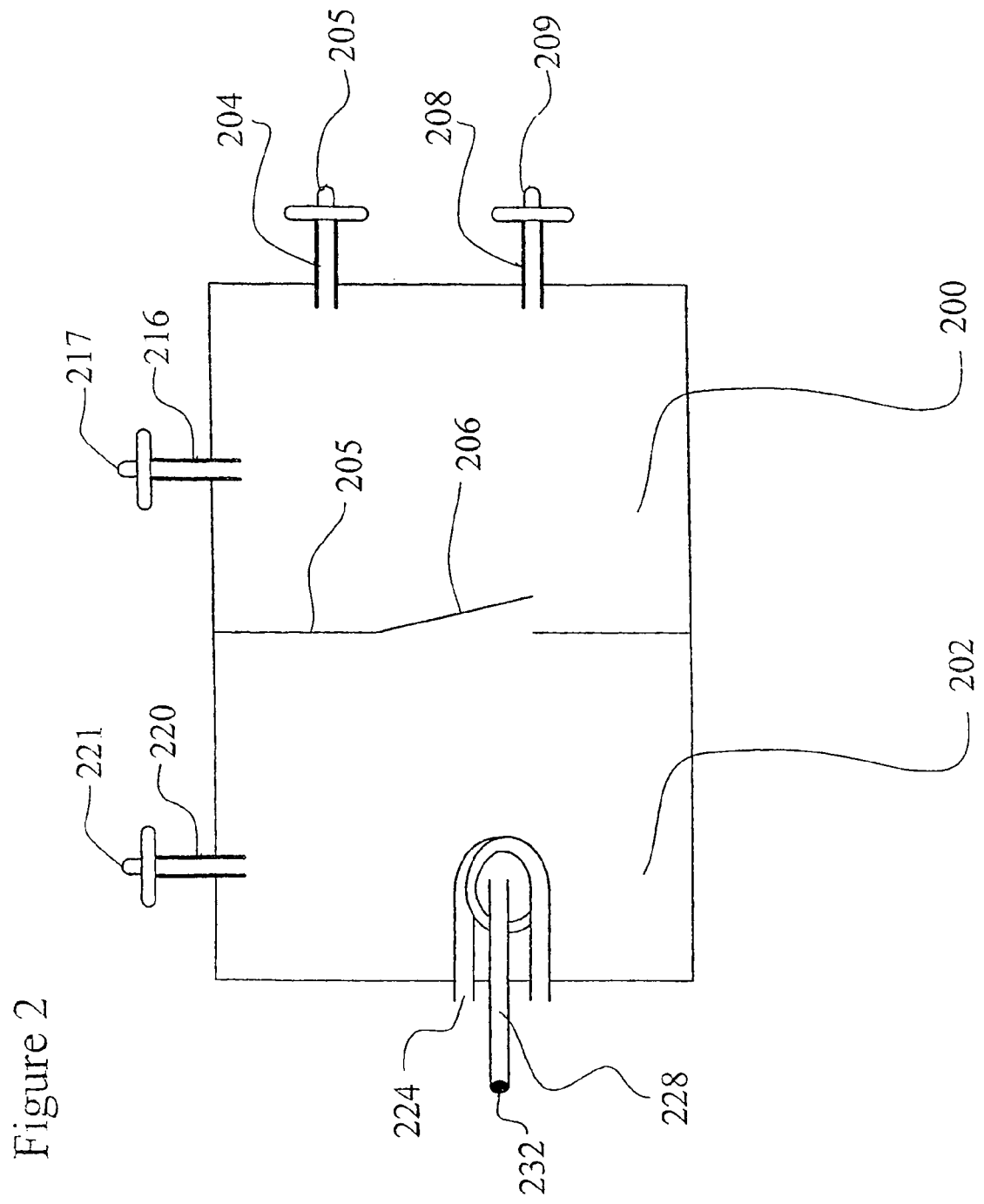
FIG. 2 is an overhead view of the interior of a presently-preferred embodiment of a parasite production chamber showing the inlet and outlet tubes.

FIG. 2 is a cross-sectional view of the interior of a presently-preferred embodiment of the present invention specifically showing the tubes that extend to the interior of the parasite production chamber. The interior of the parasite production chamber may be divided into two portions by a wall 205 that preferably contains a closable door 206 between the two portions. The two portions of the parasite production chamber may be conceived of as an insect rearing portion 200 and a blood meal portion 202. An air inlet tube 204 allows humidified air to be forced into the parasite production chamber thus providing oxygen to the system as well as creating a positive pressure gradient from the internal to external environment that inhibits microbes from contaminating the system. The air inlet tube 204 may also deliver anoxic gas to the system to sacrifice the parasite infected insects for easy collection as will be discussed herein below. An air outlet tube 208 allows forced air to vent from the interior of the parasite production chamber. Both the air inlet tube 204 and the air outlet tube 208 preferably have a micro-pore filter 205 209 attached to their exterior end to prevent air borne microbial contamination to pass from the external environment to the interior of the parasite production chamber.

The presently-preferred embodiment of the present invention displayed in FIG. 2 further discloses a tube 216 useful for introduction of larva rearing broth into the insect rearing portion 200 of the parasite production chamber. The broth introduction tube 216 also may contain a micro-pore filter 217 for the filtering of the broth. The larva rearing broth that is used within the context of the present invention may be synthetic or semi-synthetic broth, as is dictated by the particular insect that is being grown. The broth introduction tube 216 allows larva rearing broth to be introduced into the larva rearing reservoir as described herein below.

FIG. 2 further displays a water introduction tube 220 for the introduction of water into an egg retaining reservoir as described herein below. The water introduction tube 220 preferably contains a micro-pore filter 221 which allows water to be sterilely filtered prior to introduction into the egg retaining reservoir.

FIG. 2 also discloses a blood warming tube 224. Both ends of the blood warming tube 224 preferably extend from the exterior of the parasite production chamber and both ends are open to the external environment. The blood warming tube 224 serves as a warm water heating coil to attract adult female mosquitoes into the blood meal portion 202 of the parasite production chamber and to warm the infectious blood meal as discussed herein below. FIG. 2 further discloses a blood introduction tube 228 which acts as a conduit for infectious blood to travel into the blood meal portion 202 of the apparatus for consumption by the insects. The exterior end of the blood introduction tube 228 is preferably closed by an air-tight latex or rubber plug 232.

The latex or rubber plug 232 on the exterior end of the blood introduction tube 228 allows an infectious blood meal to be aseptically injected through the plug 232 by a needle attached to a syringe.

Figure 3:
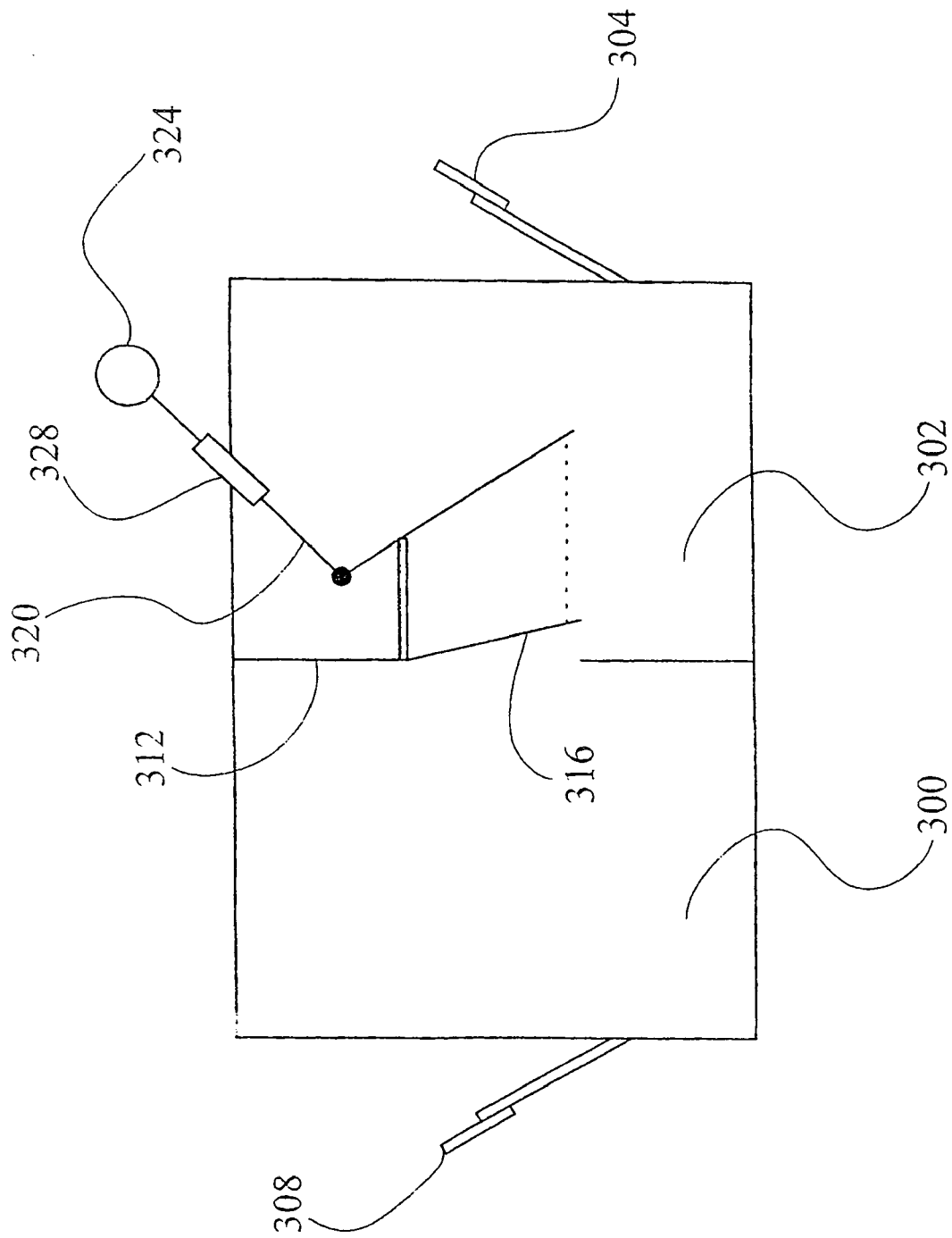
FIG. 3 is an overhead view of the interior of a presently-preferred embodiment of a parasite production chamber showing the ports and points of mechanical access.

The outer walls of a presently preferred parasite production chamber of the present invention include a series of ports and physical access points as shown FIG. 3. Each port is preferably closed by a tightly fitting hatch, gasket, and latch to provide an air tight seal to the interior of the parasite production chamber. In other preferred embodiments, ports could be designed with a tightly fitting rubber or latex plug as previously described. To improve the air tight seal, a non-volatile and non-toxic lubricant such as glycerol can be coated on the gasket. Each port is designed and located to serve a specific purpose in parasite production and hence its diameter can vary according to the demands of the insect being grown. An egg transfer port 304 preferably opens into the insect rearing portion 302 of the parasite production chamber. The egg transfer port 304 preferably allows surface sterilized eggs to be aseptically transferred by sterile pipette onto a semi-submersible float in the larva rearing reservoir as described herein below. An insect removal port 308 preferably opens to the blood meal portion 300 of the parasite production chamber. The insect removal port 308 preferably allows infected insects to be collected after they have been sacrificed at the end of the production run.

Internally, the parasite production chamber of the present invention is preferably sub-divided into an insect rearing portion 302 and an blood meal portion 300 by a partition 312, which may be a solid wall or a mesh screen. The partition 312 preferably has a door 316 between the insect rearing portion 302 and the blood meal portion 300 that can be opened or closed via a mechanical linkage rod 320. This device may also be a screw turn or other mechanical device used to open and close the door 316. The mechanical linkage rod 320 is preferably operated by manipulating a lever 324 on the exterior surface of the parasite production chamber. The mechanical linkage rod 320 is preferably enclosed in a tight fitting rubber or metal grommet 328 lubricated with a non-volatile and non-toxic lubricant such as glycerol where the mechanical linkage rod 320 passes through the exterior wall into the interior of the apparatus. This grommet 328 helps to maintain sterility inside the parasite production chamber.

Figure 4:
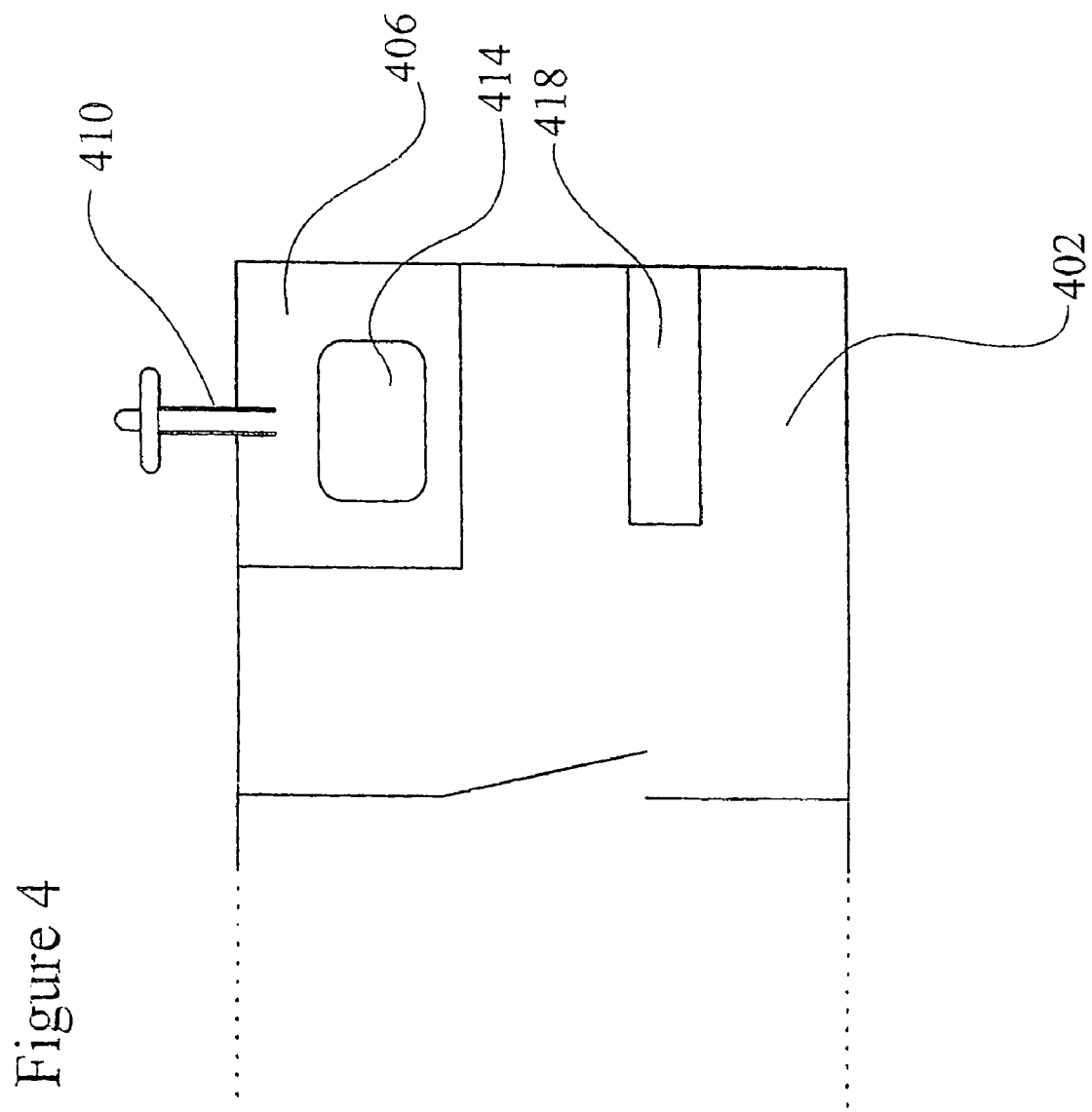
FIG. 4 is an overhead view of the interior of the insect rearing portion of a presently-preferred embodiment of a parasite production chamber.

As displayed in FIG. 4, the insect rearing portion 402 of the parasite production chamber contains multiple specialized components that are capable of supporting the aseptic aquatic life stages of the insect's eggs, larvae, pupae and adult. A larva rearing reservoir 406 rests on the bottom of the apparatus and is designed to hold the sterile larvae rearing broth delivered by the broth introduction tube 410 as described hereinabove. A semi-submersible float 414 preferably rests on the bottom of the larva rearing reservoir 406. When larva rearing broth partially fills the larva rearing reservoir 406, the semi-submersible float 414 rests just below the fluid surface. Surface sterilized eggs of *Anopheles* mosquitoes no longer float and will perish if allowed to sink too deeply into the larvae rearing broth. The semi-submersible float 414 preferably supports the surface sterilized eggs just below the surface of the fluid insuring viability. As the float 414 is semi-submersible, the LI larvae are not prevented from swimming to other locations within the larva rearing reservoir 406. The insect rearing portion 402 of the apparatus also contains a sugar feeding reservoir 418. The sugar feeding reservoir 418 is preferably a small sugar trough with a landing pad of mesh screen that provides the adult insects with a nutritive substance after hatching from pupae. Alternatively, the sugar feeding reservoir may be a wick-based sugar feeding system as described herein below. Since sugar is highly hydrophilic and is partially dissolved in conditions of high humidity and warm temperatures, the landing pad allows the adult insects to land and feed on the sugar through the mesh without becoming stuck.

Figure 5:
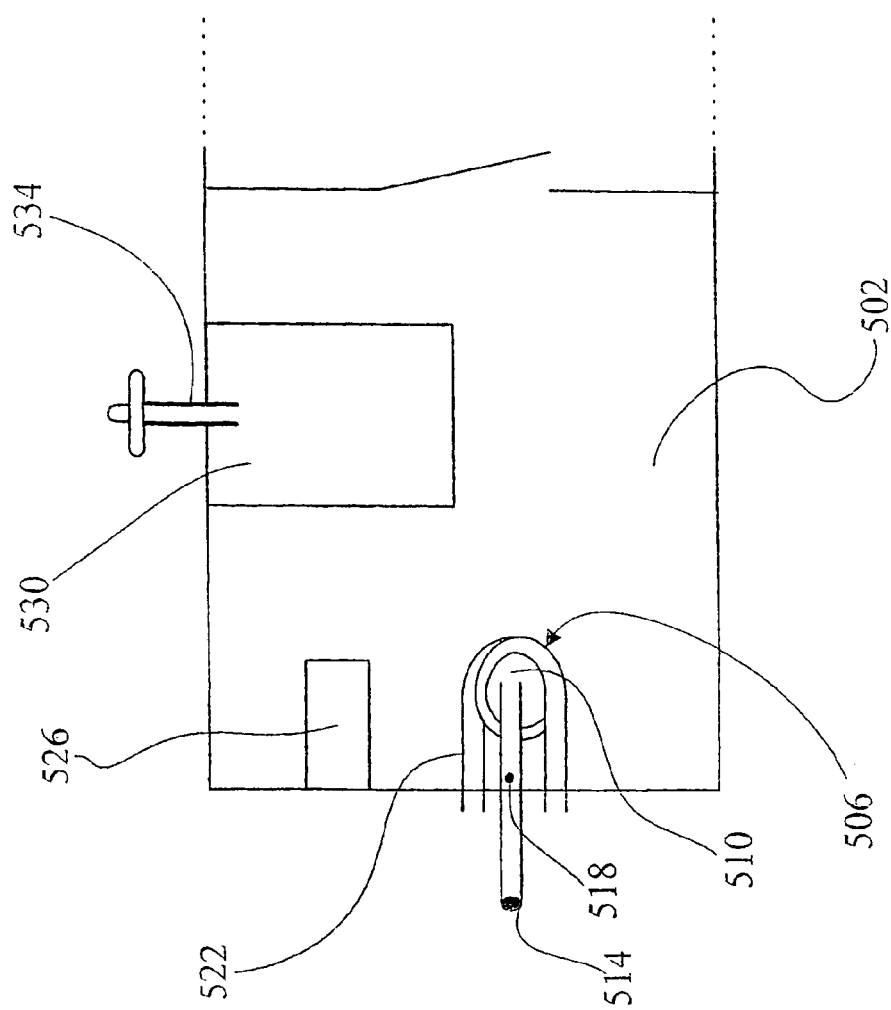
FIG. 5 is an overhead view of the interior of the blood meal portion of a presently-preferred embodiment of a parasite production chamber.

The blood meal portion 502 of the parasite production chamber is displayed in FIG. 5. Within the blood meal portion 502, specialized components support the production of aseptic parasites and insect hosts, including *Plasmodium* species sporozoites within the adult female mosquito. A blood feeding station 506 is comprised of a blood reservoir 510 covered by thin membrane or fine mesh screen as described in greater detail below. The blood reservoir 510 can be a Rutledge type feeder or any other type of blood meal device. The blood reservoir 510 is connected to the blood introduction tube 514 that extends to the exterior of the parasite production chamber. As previously described, the blood heating tube 522 is a heating coil that circulates warm water into and out of the apparatus. The coil of the blood heating tube 522 preferably encircles the blood reservoir 510 or circulates warm water within a Rutledge type feeder to heat the blood. When the present invention is utilized to produce *Plasmodium* sporozoites and *Anopheles* mosquitoes, the operation of the blood reservoir 510 can function to segregate female from male mosquitoes and also provides an infectious blood meal to the female mosquitoes for the cyclo-propagative development of aseptic *Plasmodium* species parasites.

FIG. 5 further discloses a sugar feeding reservoir 526 that is similar to the sugar feeding reservoir found in the insect rearing portion of the parasite production chamber. While this aspect of the present invention is described using sugar as an example, any nutrition source may be used. The sugar feeding reservoir 526 is preferably a small sugar trough with a landing pad of mesh screen that provides the adult insects with a nutritive substance. The sugar feeding reservoir 526 may be replaced by a wick-based feeding system as described herein below.

Following a blood meal, female *Anopheles* mosquitoes will develop their eggs in approximately 48 hours. To allow ovipositing of these eggs, an egg oviposition reservoir 530 rests on the bottom of the blood meal portion of the parasite production chamber. The egg oviposition reservoir 530 is designed to be partially filled with sterile water as delivered by the water introduction tube 534.

Figure 6A:
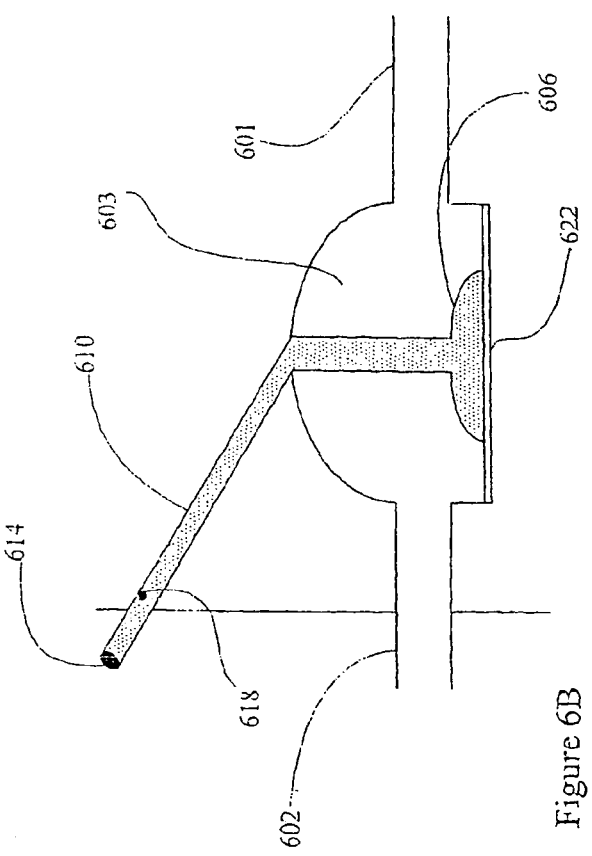
FIG. 6A is a view of a blood feeding station of the present invention.

FIG. 6 displays two preferred embodiments of a blood feeding station. FIG. 6A displays the blood warming tube 602 that allows warm water to be transferred from the exterior to the interior of the parasite production chamber for warming of the infectious blood meal. The warm water is then transferred back out of the parasite production chamber by another tube 601. The blood warming tube 602 expands into a chamber 603 that surrounds a blood feeding chamber 606. The blood introduction tube 610 extends to the exterior of the apparatus. The exterior end of the blood introduction tube 610 contains a latex or rubber plug 614. During operation of the blood feeding station, infectious blood is injected through the plug 614 into the blood introduction tube 610. The blood travels down the blood introduction tube 610 into the blood feeding chamber 606 where it spreads over the membrane 622 that lines the bottom of the blood feeding chamber 606. The membrane 622 is such that it is able to be pierced by the proboscis of the adult female mosquito, thus providing an infectious blood meal to the mosquito. During heating of the blood, the volume of gas within the blood feeding chamber 606 expands. During heat sterilization of the blood feeding chamber 606 the volume of gas within the blood feeding chamber 606 expands. In order to not damage either the membrane 622 or the plug 614, a vent 618 is included on the superior aspect of the blood introduction tube 610 to allow for relief of any built up pressure.

Figure 6B:
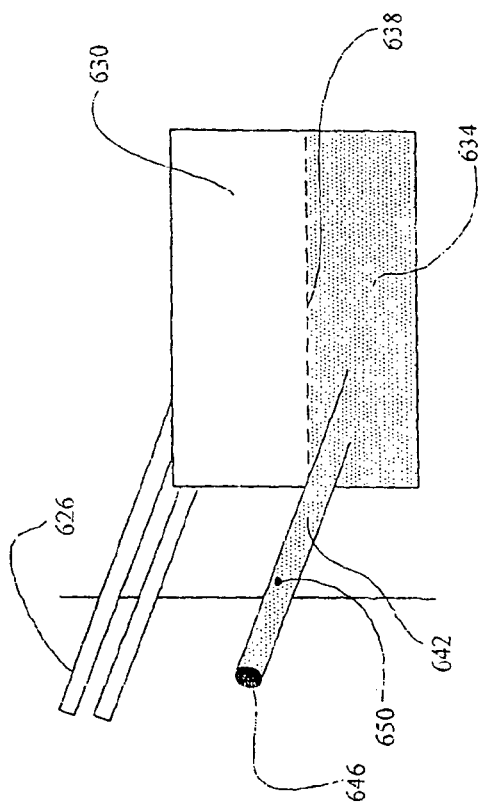
FIG. 6B is a view of a blood-feeding station of the present invention.

Another embodiment of a blood feeding station is disclosed in FIG. 6B. Blood warming tubes 626 extend from the exterior to the interior of the parasite production chamber. In this embodiment, the blood warming tubes 626 contact a blood reservoir 634 such that when warm water is pumped through the blood warming tubes 626, the blood within the blood reservoir 634 is heated. There are multiple ways of achieving this heating, including the blood heating tubes 626 encircling the blood reservoir 634, the blood heating tubes 626 establishing contact underneath the blood reservoir 634, and the blood heating tubes 626 forming a heating reservoir 630 juxtaposed to the blood reservoir 634. One of skill in the art would recognize many such ways of heating the blood meal. The blood has a membrane or mesh 638 over top of it to provide adult insects (e.g., adult female *Anopheles* mosquitoes) support when they take an infectious blood meal. Infectious blood may be injected into the blood introduction tube 642 through a rubber or latex plug 646 located in the exterior end of the blood introduction tube 642. The blood introduction tube 642 may also contain a vent 650 that may be used to relieve pressure that may build up during autoclaving sterilization.

Figure 7A:
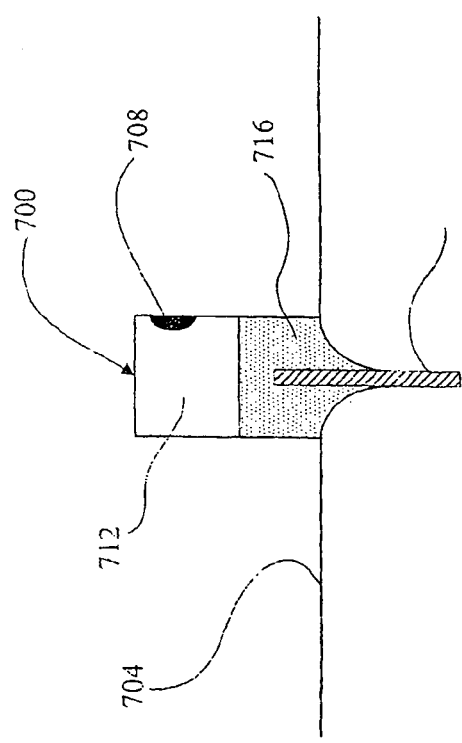
FIG. 7A is a view of a wick-based sugar feeder of the present invention.

FIG. 7A discloses a presently-preferred wick-based sugar feeder 700 to be used within the apparatuses of the present invention. The sugar feeder preferably rests on the top of the apparatus of the present invention 704. The lower portion of the sugar feeder 700 preferably extends into the interior of the apparatus of the present invention with an air tight seal. The upper portion of the sugar feeder 700 preferably contains a rubber or latex plug 708 through which sugar solution 716 be injected into a reservoir 712 in the sugar feeder 700. The sugar solution 716 drains to the bottom of the reservoir 712 into a wick 720 that extends to the interior of apparatus. Insects may then land on the wick 720 and to consume the sugar solution 716 that saturates the wick 720.

Figure 7B:
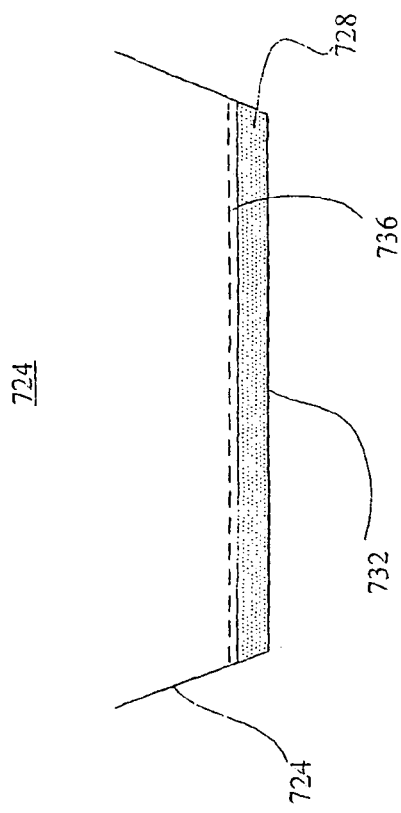
FIG. 7B is a view of a trough-based sugar feeder of the present invention.
Figure 8A:
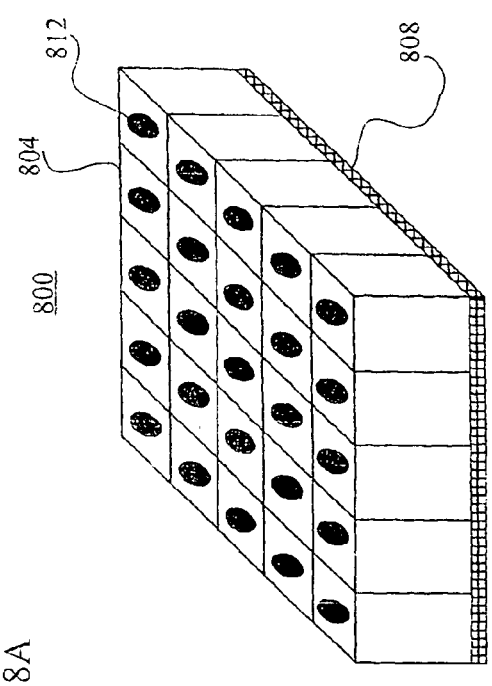
FIG. 8A is a view of a hematophagous insect bite chamber array of the present invention.
Figure 8B:
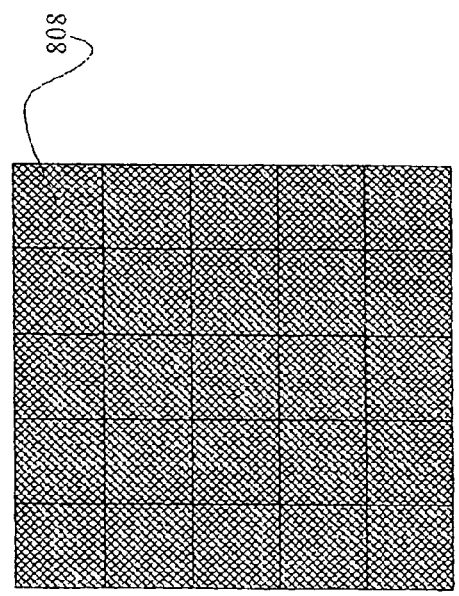
FIG. 8B is a bottom view of a hematophagous insect bite chamber array of the present invention.

FIG. 7B discloses a presently-preferred trough-based sugar feeder 724 to be used within the apparatuses of the present invention. Sugar 728 is preferably placed in the base of the trough 732 with a mesh membrane 736 over top which acts as a landing pad. Since the sugar 728 is highly hydrophilic and is partially dissolved in conditions of high humidity and warm temperature, the mesh membrane 736 allows the adult insects to land and feed on the sugar 728 through the mesh without becoming stuck.

Though not specifically described, additional tubes, reservoirs, ports, and subsections may be added to adapt the parasite production chamber of the present invention to the production of various parasite/insect pairs. If desired, reservoirs can be drained with additional tubes after the function of the reservoir has been completed.

The operation of the above-described parasite production chamber for the aseptic production of *Plasmodium* sporozoites and *Anopheles* mosquitoes will now be described. Initially, the entire parasite production chamber is sterilized either by irradiation, chemical treatment, autoclaving, or other sterilization process known in the art and sterility is maintained hereafter. The various sugar feeding reservoirs are filled with sugar. The door between the insect rearing portion of the parasite production chamber and the blood meal portion of the parasite production chamber is closed so as to limit the initial movement of the immature mosquitoes.

The larva rearing reservoir is partially filled with sterile larva rearing broth through the larva broth introduction tube and the semi-submersible float will come to rest just below the surface of the broth. Surface-sterilized, *Anopheles* eggs are then placed onto the semi-submersible float through the egg access port. The temperature and humidity of the interior of the parasite production chamber is maintained at conditions that promote the development of the *Anopheles* eggs. As the eggs develop into larvae, the larvae swim off of the float and swim around in the larva rearing chamber.

After the larvae develop into pupae, the adults hatch from the pupae and are free to fly around the interior of the insect rearing portion of the apparatus feeding on the sugar that is located in the sugar feeding reservoir. After the mosquitoes have grown into adults, the female mosquitoes are then ready to he fed an infectious gametocyte blood meal in the blood meal portion of the parasite production chamber.

To begin the blood meal feeding procedure, warm water is forced through the inlet of the blood warming tube that coils around or through the blood feeding reservoir. The door in the partition separating the insect rearing portion and the blood meal portion of the parasite production chamber is opened by means of a lever. The female *Anopheles* mosquitoes are selectively attracted to the warm source and fly through the hatch, thus effectively segregating female and male mosquitoes. After a period of time, the hatch is then closed. Infectious blood that contains gametocytes of the *Plasmodium* parasite is injected through the exterior latex or rubber port of the blood introduction tube. The blood runs down the blood introduction tube and spreads over the membrane or under the mesh screen depending on the blood feeding system that is being employed. The female *Anopheles* mosquitoes then feed on infectious gametocyte blood.

After a sufficient period of time for sporozoites to develop, anoxic sterilely filtered gas is blown into the apparatus from the air inlet tube. This stuns the mosquitoes and they fall to the bottom of the apparatus. The insect removal port is opened and a sterile vacuum tube is inserted and the female mosquitoes are aseptically removed from the blood meal portion of the parasite production chamber. These female mosquitoes are then a source of aseptic *Plasmodium* sporozoites.

The operation of the parasite production chamber of the present invention may he better understood with the description of the following example.

EXAMPLE

The sugar feeding reservoirs are charged with a small amount of sucrose. Several Milliliters of a thick suspension of fine particulate solution suitable for ingestion by *Anopheles* larvae is mixed with 300 milliliters of water and is placed into the larva rearing reservoir of the system. The door between the insect rearing portion and the blood meal portion is closed and the container is autoclaved at 120 degrees Celsius at 30 pounds per square inch pressure for 30 minutes. The device is allowed to slowly cool to room temperature. Semi-synthetic larva rearing broth is then sterilely filtered into the larva rearing reservoir to replace or replenish any heat labile nutrients.

Approximately 100 Ancphe7es stephensi eggs which have been surface sterilized by agitating for 10 minutes in 70 percent ethanol and 1 percent benzalkonium chloride and washed are transferred into the system with a pipette using sterile technique via the egg transfer port. The surface sterilized eggs, no longer buoyant, are discharged onto a semi submersible float. The apparatus is transferred to a room with a temperature of 28 degrees Celsius and a diurnal light phase of light:dark 14/10. Low volume air is sterilely filtered into the apparatus to maintain a positive pressure gradient inside the system.

The eggs hatch and larva and pupae form in the larva rearing reservoir with adult mosquitoes appearing in approximately 9 days. The adult mosquitoes derive nutrition from a sterile sugar source(s) within the device.

The door between the insect rearing portion and the blood meal portion of the apparatus is then opened approximately three days after emerging from the pupae. A warmed feeding station in the blood meal portion of the apparatus induces adult female mosquitoes to self segregate from males by flying through the opened door to seek an obligate blood meal. The males are not attracted to the heat source and do not seek a blood meal. After an amount of time sufficient for separation of males and females, the hatch is closed.

After feeding on the infectious *Plasmodium* gametocyte blood meal, the infected gravid female mosquitoes are provided sterile water for egg laying and derive nutrition from a sterile sugar source. The *Plasmodium* sporozoites fully develop in the female *Anopheles* mosquito approximately 14 days after the infectious blood meal. At this time, micro-filtered anoxic gas is discharged into the apparatus, thus stunning the mosquitoes. The stunned female mosquitoes are then removed via the insect removal port and are processed to obtain the aseptic *Plasmodium* sporozoites, which may be used in the development of, and the immunogen of, an attenuated whole sporozoite vaccine.

Best Mode

FIG. 10 shows the best mode contemplated by the inventors of carrying out the invention. In this mode, the larval or insect rearing first sub-chamber 801 is separable and independent from the adult mating, blood meal feeding and infection second sub-chamber 901—each sub-chamber having an independently controllable air space. All of the components of this mode are sterilizable, preferably by autoclave. The first and second sub-chambers are preferably fabricated from clear glass or temperature-resistant plastic, most preferably from glass. In the embodiment shown, the insect-rearing sub-chamber 801 is generally conical in shape with a wide mouth 803 adapted to receive a sealing cap 930 or a coupler 940, described below. Alternatively, the cap can be adapted to contain an opening for passage of filtered air or adapted to include a micro-filter for air (not shown). It is important to note however, that an essential feature of the chamber and each independent sub-sub-chamber is that the air passage into the chamber is controllable so as to prevent escape of insects and to insure sterility of incoming air. This is referred to as "air-controlled" or a controllable air space. Preferably, the mouth is 1 to 3 inches in diameter, most preferably adapted to receive a standard 70 mm solid screw cap 930. Optionally, this first sub-chamber 901 can also contain various sealable ports 802 and tubes (e.g. similar to 124 and 128) as disclosed above and illustrated in FIGS. 1 through 4 herein, e.g. to provide for filtered air circulation. The size of the first sub-chamber can vary depending on the number of insects to be raised. Preferably the diameter of the first sub-chamber is 2 to 18 inches, most preferably 10 inches, and 2 to 12 inches in height, preferably 6 to 7 inches. A desirable feature of this sub-chamber is the shallow angle of slope of the conical walls. Since flying insects prefer a rough surface to alight upon, this steep, smooth surface helps to funnel the insects toward the neck 803 of the sub-chamber for passage into the other sub-chamber 901.

The blood-meal second chamber 901 is adapted to contain an upper 909 and lower 902 neck and mouth. The upper and lower mouths are the same size as the mouth 803 on the first sub-chamber and similarly adapted to receive the same sealing cap 930. In a preferred embodiment, the second sub-chamber is cylindrical with a diameter of 2 to 18 inches, most preferably 10 inches (or similar to the base dimension of the first sub-chamber with which the unit is used). The height of this sub-chamber is 2 to 14 inches, most preferably 6 inches. Similar to the first sub-chamber the second sub-chamber may also be fabricated to contain various sealable ports and tubes such as those shown 905. Preferably, some of these ports are GL-14 with Luer-loc adapters. Optionally, the second sub-chamber may also contain a larger port 906, preferably 1 to 3 inches in diameter, most preferably adapted to receive a 45 mm solid sealing cap. This port is useful for providing access to the interior of the sub-chamber for the sampling, and other manipulations described herein. Constrictions 903 are provided within the upper 909 and lower 902 necks of the second sub-chamber. Preferably, the constrictions 903 are 360 degrees around the inner perimeter of the necks. The constrictions 903 provide a lip for limiting and locating various other elements when inserted into the necks 902 and 909 of the sub-chamber 901, e.g. a fine-mesh barrier 950 to prevent insect escape. The lip provides a means for maintaining an air-controlled neck 909 after insertion of said elements.

Flying insects prefer a rough surface to alight upon. Therefore, a portion of the interior surface of sub-chamber 901 is abraded 911. This can be accomplished through sandblasting, chemical etching or the like.

The first 801 and second 901 sub-chambers are joinable by means of a coupler 941. The coupler is a double cap adapted to fit both the neck 803 of sub-chamber 801 and the neck 902 of sub-chamber 901. The coupler has an axial passage 941, preferably 1 to 2 inches in diameter, providing communication between the two sub-chambers and allowing for passage of insects from sub-chamber 1 to sub-chamber 2 as described.

The insertable/removable fine-mesh barrier 950 is a dish adapted with a fine-mesh bottom 951 and a lip 952 adapted to rest upon constriction 903. The barrier 950 is useful to prevent escape of flying insects.

Figure 10:
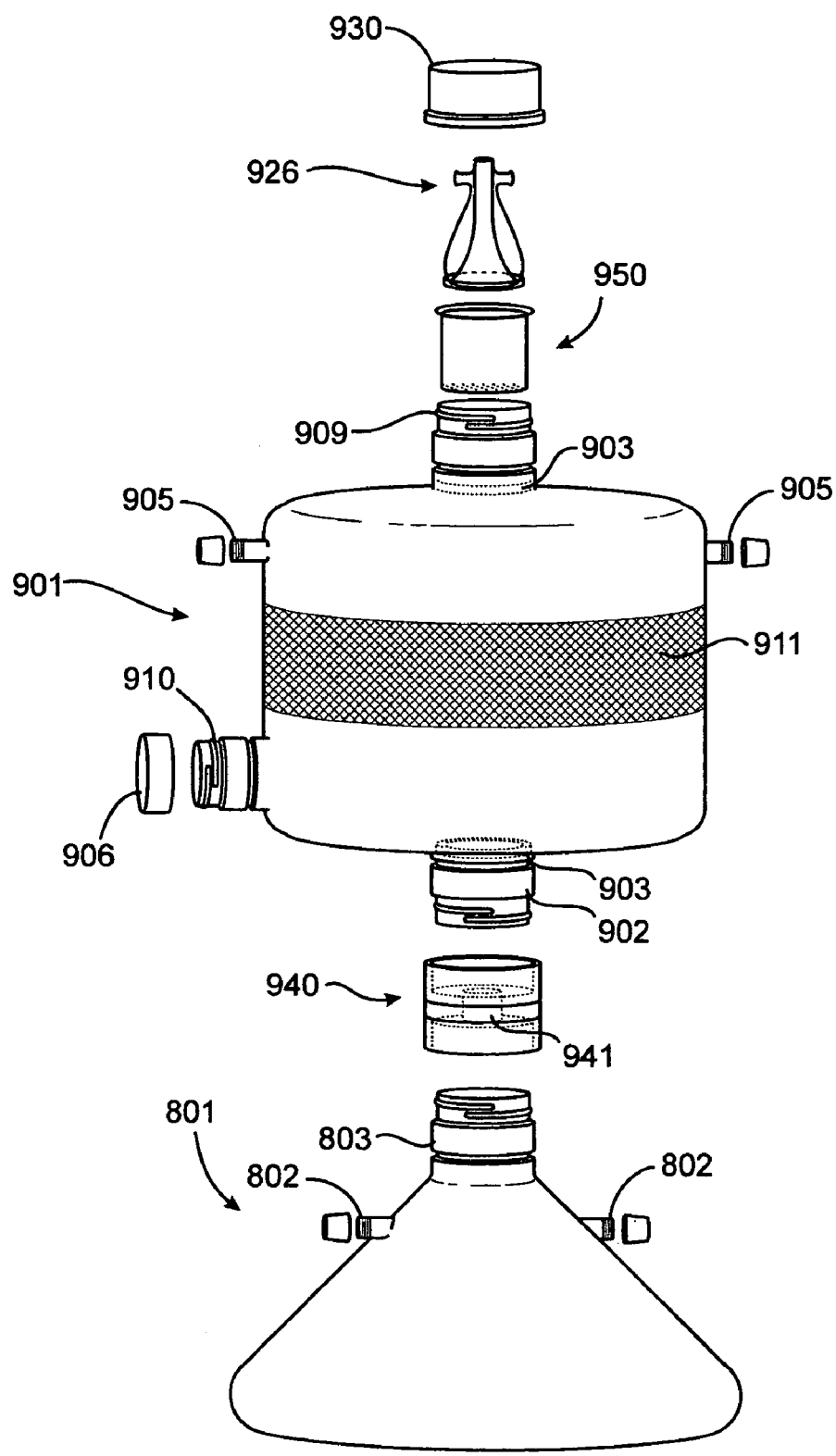
FIG. 10 is a side view of an embodiment of a modular mode of an insect rearing apparatus of the present invention.
Figure 10B:
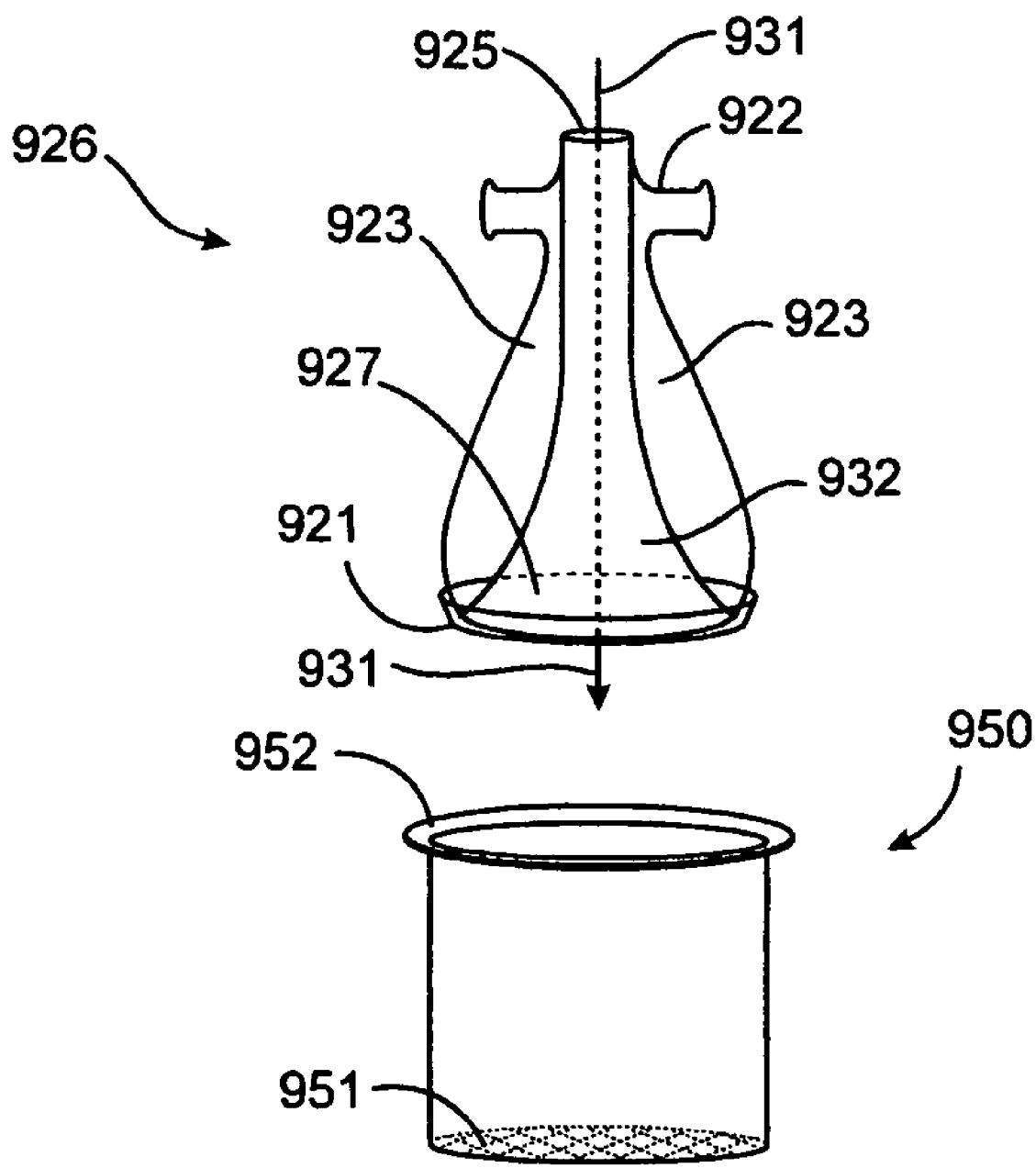
FIG. 10B is an expanded view of the blood-feeding station and wire mesh barrier of the modular mode of an insect rearing apparatus, both shown in FIG. 10.

The insertable/removable blood feeding station 926 shown in the figure is similar to those described above and shown in FIG. 6, but adapted to fit within the necks 909 and 902 and upon the fine mesh barrier 950 which is locatable upon the constricting lips 903 of sub-chamber 901. This station is shown in more detail in FIG. 10B. The feeder is a hollow fluted tube with an interior lumen 932 open at both ends as depicted 931. A water jacket 923 surrounds the lumen and is adapted with ports 922 for the circulation of warm water. The lower opening 927 of the lumen is fitted with a removable membrane 921 penetrable by feeding mosquitoes. The lower opening 927 is circular and, along with membrane 921, can be placed to rest upon the fine-mesh 951 of barrier 950, which in turn rests upon lip 903 within a neck of sub-chamber 901. Alternatively, the membrane 921 can be replaced with a fine stainless steel or plastic mesh of a pore size smaller than an adult mosquito to prevent passage of the mosquito through the mesh.

Operation

It will be appreciated that this mode functions the same as the modes described above, but with the added convenience that each sub-chamber can be handled and operated independently, or combined to another sub-chamber, as desired or necessary for enhanced system performance. Alternatively, all steps could be performed in a single sub-chamber without insect transfer. Other advantages will be apparent from consideration of the method of using this mode.

Larval rearing broth with a semi-submersible float 419 is added to sub-chamber 801, which serves as a larva rearing reservoir 406 (FIG. 4). In yet another embodiment, a separate larval rearing broth reservoir 406 is permanently adapted within sub-chamber 801. The sub-chamber is capped with a cap adapted to allow for the passage of filtered air. Alternatively, filtered sterile air is passaged through ports 802. The sub-chamber is then autoclaved to sterilize the entire assembly. After cooling, the cap 930 is aseptically opened and surface-sterilized mosquito eggs are inserted through the neck 803 of the sub-chamber onto the float 419. Preferably the number of insect eggs is 10 to 10,000, most preferably 250 to 750. The sub-chamber 801 is then placed into a light, temperature and humidity controlled insectary as disclosed.

The blood-meal sub-chamber 901, with fine-mesh barrier 950 placed in neck 909 and caps 930 on the necks 902 and 909, is similarly prepared by autoclaving. At the start of larval pupation, the cap 930 is removed from neck 902 and blood-meal sub-chamber 901 is coupled to rearing sub-chamber 801 by attaching coupler 940 first to the top of rearing sub-chamber 803 and then attaching the bottom of blood-meal sub-chamber 902 to the coupler 940. The full assembly is returned to the insectary.

Emerged adults fly up toward the top of sub-chamber 801 and are focused toward the neck 803 by the geometry and smooth steep walls of sub-chamber 801 as described. Adults are thus encouraged to fly through the orifice 941 of the connector 940 and into the second sub-chamber 901 by a sugar feeding station 526 (FIG. 5) placed in sub chamber 901. Alternatively, a sugar-water meal may be provided by placing a sterilized sugar-water impregnated cotton ball on top of wire mesh barrier 950. Other attractant methods such as providing a hood to darken the area of sub-chamber 901 or the use of chemical attractants may also be utilized. Once enticed into blood-meal sub-chamber 901, the mosquitoes grip the rough surface 911 provided to rest. Mating occurs and adult mosquitoes become quiescent.

Subsequently, the sub-chambers are aseptically separated and the lower opening 902 of sub-chamber 901 is capped with cap 930. At the appropriate time, the blood-meal feeding station 926, with membrane 921 attached, is inserted in upper neck 909 by removing cap 930 and placed on the fine mesh 951 of barrier. The blood feeding station 926 can then be supplied with circulating warm water into the water jacket 923 through tubes 922. *Plasmodium* species infected blood is then provided through orifice 925 into lumen 932. The blood pools upon the top side of membrane 921. Upon completion of the blood meal, the feeder 926 is removed and the cap 930 is replaced. The barrier 950 which is left in place prevents the infected mosquitoes from escaping sub-chamber 901 during this operation. Filtered air is circulated through orifices 905.

It will be noted that multiple sub-chamber 901 units could be attached in series by inverting a first unit containing mosquitoes and attaching additional units by means of coupler 940. The movement of mosquitoes from one sub-chamber 901 to another sub-chamber 901 can be accomplished by use of attractants as described above. This allows the reduction and or addition of mosquitoes from one chamber to another as is desired by the operator.

Subsequently, a sub-chamber 901 with infected mosquitoes may be exposed to irradiation or other means described herein to attenuate the *Plasmodium* sporozoites. Mosquitoes are then collected at the appropriate time by means of a suctioning tube inserted through neck 902, 909, or 904 after removal of cap 930, fine mesh screen 950 or cap 906 as necessary and desired. Though irradiating the infected mosquitoes prior to removal from sub-chamber 901 is not absolutely necessary, irradiation attenuates the parasites in-vivo and will ultimately kill the mosquitoes. As such, accidental escape of irradiated-infected mosquitoes at this stage of the operation will not result in accidental transmission of infectious *Plasmodium* parasites to humans or animals. After irradiated-infected mosquitoes are removed from sub-chamber 901, the salivary glands of the female mosquitoes are dissected out as disclosed and the salivary glands containing attenuated *Plasmodium* sporozoites are pooled for use as a vaccine component.

A central feature of this mode is its modular features for the rearing of aseptic insects and the production of aseptic parasites. One skilled in the art can readily recognize that the modular modes of this system and its operation are adaptable to meet a wide variety of research, quality-control, and vaccine production purposes. As such, the steps described in the operation of this invention can be readily modified to meet the diverse needs of the operator. The sequential steps provided above are meant to be illustrative for the purpose of teaching one skilled in the art a particular application in the constellation of necessary and beneficial applications that this invention offers. A skilled operator will readily appreciate the benefits of this invention's unitary applications as well as modular applications. For instance, sub-chambers 801 and 901 can be joined with coupler 940 and autoclaved together, or separately. As previously discussed, multiple units of sub-chamber 901 can be added in series.

The modular aspect of this mode enables many operational permutations. Preparing and sterilizing sub-chamber 801 alone allows the operator to observe the chamber for microbial contamination before attaching to sub-chamber 901, and may be preferable for vaccine quality control measures during vaccine production. Combining sub-chambers 801 and 901 at the start may be preferable for experiments in life-cycle, infectivity, yield and environmental studies. Combining sub-chamber 901 units in series may be preferable to adjust mosquito numbers by use of attractants to reduce overcrowding, increase mosquito numbers, or sample from one or several mosquito occupied sub-chambers. Alternatively, sequential sub-chamber 901 units can be attached to a particular sub-chamber 801 unit to extract a desired number of mosquitoes into each sub-chamber 901 units allowing for efficient use of available pupa and distribution of mosquitoes. When sufficient numbers of adult mosquitoes are present in sub-chamber 901, sub-chamber 801 can be detached and sub-chamber 901 would serve as a modular unit capable of further processes as described while sub-chamber 801 would be reincubated to generate more insects of sufficient maturity, attached to another sub-chamber 901 to collect more adult mosquitoes or reused or replenished with more eggs as described.

In a variation of the described process, the operator's ability to manually extract or move insect-life stages from one modular component to another is substituted for the ability of the insects to move from one modular assembly to another by self locomotion.

Aseptic manipulation of this invention is important in many phases of its operation, and one skilled in the art can readily recognize various techniques to achieve and maintain asepsis by the use chemicals, biological hoods, aseptic technique and the like. As such, a detailed description of the steps necessary for concurrent and sequential aseptic conditions and techniques in the use of this invention, or its modular components, is not provided but is readily deducible by one skilled in the art.

An additional aspect of the present invention includes a hematophagous insect biting chamber array (FIG. 8A, 8B). This apparatus is useful for the study of the biting behavior and reactogenic/allergic potential of individual hematophagous insects. These studies are useful in the selective breeding and genetic manipulation of hematophagous insect populations.

The hematophagous insect biting chamber array is preferably a three dimensional rectangular structure with two large parallel surface planes of rectangular shape. The interior of the hematophagous insect biting chamber array 800 preferably is subdivided into multiple sub-chambers 804 of similar dimensions. Each sub-chamber extends the height of the array and is capable of housing an individual insect.

On one side of the array, the surface is a metal mesh 808 that prevents the escape of the insect species under study. A plastic cover is arranged so that the mesh 808 can be covered to prevent the insects from inadvertently biting the operator or having wind drafts alter the internal environment of the sub-chambers 804. The mesh 808 thus allows insects to probe, bite, or feed on the skin of a human or animal when the hematophagous insect biting chamber array 800 is juxtaposed to a patch of skin. The mesh 808 is preferably attached and supported by the solid outside perimeter of the hematophagous insect biting chamber array and the solid interior perimeter of the sub-chambers.

On the side of the array opposite that of the mesh 808, individual hatches 812 are attached to the outside perimeter of each sub-chamber 804 so as to allow access to each sub-chamber 804 individually. The sub-chambers 804 thus allow individual insects to be housed separately. In such an arrangement, each insect is not subjected to interference by other insects, and variables in the environment such as light exposure, color of the environment, chemical environment, etc. may be manipulated independently for each insect.

To operate the hematophagous insect biting chamber array 800, individual insects are placed into the sub-chambers 804 and the hatches 812 are secured. The plastic covering that is over the mesh 808 is removed and the mesh 808 side of the array is placed in contact with the skin of a human or other animal. Using a protocol that may be particularly developed for each insect species that is to be tested, the insects are allowed to probe and feed for variable lengths of time. The structure of the hematophagous insect biting chamber array 800 is such that it allows the same patch of skin to be exposed to the same insect multiple times.

An additional aspect of the present invention is a strain of insects, such as mosquitoes, that is hypoallergenic to humans or other animals.

The production of hypoallergenic insects may be accomplished by the following procedure. A heterogeneous, genetically diverse population of a particular mosquito species is allowed to breed freely in an enclosed insectary. Gravid females are isolatedat the appropriate time in their life cycle when a blood meal is necessary to complete egg development.

A number of such female mosquitoes are then preferably placed into a subdivided rectangular container that is adapted to allow the mosquitoes access to the skin of a human or other animal while at the same time not allowing them to leave the chamber. One example of this apparatus is the hematophagous insect bite chamber array described hereinabove. Preferably, a single female mosquito occupies each chamber of the hematophagous insect bite chamber array.

The hematophagous insect bite chamber array is preferably kept under strict environmental controls such that there is limited variability in temperature, humidity, and ambient light.

A hematophagous insect bite chamber array that is loaded with female mosquitoes is then placed onto a previously prepared animal or human skin surface. Preferably, each female mosquito will be allowed access to a single, unique section of skin. Preparation of the skin may include shaving the hair from the skin of the test location and the restraint from exposure of the skin surface to soaps, creams, or other artificial substances for approximately 24-48 hours. The skin surface is preferably marked so that an experimenter can identify which female mosquito bites each section of skin.

Test subjects and animals preferably include both individual who react normally to mosquito bites as well as those who have a history of hypersensitivity to mosquito bites.

The hematophagous insect bite chamber array is preferably placed onto the skin for a short period of time to allow the mosquitoes to probe the skin in an effort to obtain a blood meal. The hematophagous insect bite chamber array is then lifted from the skin two to three times and then returned to the same spot on the skin. This preferably allows the mosquitoes to take additional probes and thereby inject more antigens from the same patch of skin. Those female mosquitoes that are not probing or engorging are identified and discarded. Each hematophagous insect bite chamber array challenge may last for approximately two sequential feeding periods of three minutes by a one minute break.

After the hematophagous insect bite chamber array challenge is completed, the skin reaction of the test human or animal is assessed at fifteen minutes, thirty minutes, one hour, two hours, twenty-four hours, and four days. Such timer periods allow for the assessment of hypersensitivity, Arthus, and delayed type hypersensitivity reactions. The assessment will include careful objective measurement of errythema, induration, and size of lesion for each mosquito at the time in question. Subjective measurements are also preferably made for pruritus at the bite sites.

Each female mosquito in a hematophagous insect bite chamber array challenge cohort that also has been shown to have probed the skin and engorged in a blood meal is rated on the development of hypersensitivity, Arthus, and delayed-type hypersensitivity reactions in the test subject. Those females with least reactigenicity are returned to a breeding chamber and allowed to lay eggs. Those shown to have high reactigenicity are discarded.

The eggs from low reactigenicity female mosquitoes are allowed to hatch and develop. Portions of these progeny are back bred to each other or allowed to breed randomly with other low reactigenicity female progeny. Certain eggs or larvae are cryopreserved for use at a later time.

At times that are determined by the experimenter, females with low reactigenicity and their progeny are preferably infected with insect borne pathogens including, but not limited to, *Plasmodium falciparum, Plasmodium vivax, Plasmodium malariae*, and *Plasmodium ovale* to insure that they retain the capacity to propagate the pathogen of interest.

The above-described procedure is preferably repeated multiple times. The result of this procedure is the development of a hypoallergenic strain of mosquitoes shown to have low or no reactigenicity in animals and humans, while retaining the ability to propagate the pathogen of interest. This mosquito strain will preferably be useful in the development of vaccines derived from the pathogens extracted from the whole body or saliva of the mosquitoes of that strain.

While this aspect of the present invention has been described using the example of mosquitoes, the same technique may be used to produce other species of hypoallergenic hematophagous insects including, but not limited to, gnats, biting flies, fleas, lice, and ticks.

An additional aspect of the present invention includes methods for the breeding of a strain of insects capable of enhanced ability to support infectious stage parasites. While this aspect of the present invention will be described with respect to the example of *Anopheles* species mosquitoes and *Plasmodium* species sporozoites, it is to be understood that the same approach would be useful for producing strains of any insects that are capable of supporting enhanced levels of infectious stage parasites.

The production of a strain of *Anopheles* mosquitoes that is capable of supporting higher burdens of *Plasmodium* sporozoites may be accomplished by the following procedure. Heterogeneous strains or a homogenous strain of *Anopheles* mosquitoes are divided into cohorts of single females and some multiple of males. Each cohort is preferably placed in an enclosed container where environmental conditions are controlled and monitored. Preferably, the conditions among the containers are consistent.

The mosquitoes are then allowed to breed. At the appropriate time in the life cycle, the females are offered a blood meal from a pool of *Plasmodium* infected blood containing either gametocytes or processed blood-containing ookinetes. The duration of feeding and other variables are controlled to insure uniformity in the environment during the blood meal process. The females mosquitoes that are not observed to be feeding and engorging on the infected blood are preferably discarded.

At the appropriate time in the mosquito life, cycle, a nutrient water broth is added to the bottom of each container. The female mosquitoes are monitored for egg laying. Those females that are not observed laying eggs are preferably discarded.

Some eggs or developing larvae are sub-divided and cryopreserved for later use in the instances where the individual characteristics in their mother's physical and/or physiological profile be deemed beneficial. By preserving some proportion of progeny in cold storage, genetic robustness and potential is maintained.

All or some portion of the eggs and larvae in each container are preferably allowed to develop. If abnormalities in some proportion of the eggs or larvae are observed, that female and her progeny are preferably discarded.

At the appropriate time in the sporozoite life cycle (approximately fourteen to sixteen days), the salivary glands from the mosquito are dissected from the head of the mosquito. The salivary glands are gently crushed and mixed into a suspension. An exact amount of the suspension is added to an exact volume of solution. The diluted suspension is transferred to a glass slide and examined under a microscope. The level of infection is graded initially as Grade 1, 2, 3, or 4 using standard methodology. As populations of mosquitoes are progressively selected, the number of sporozoites will preferably be counted.

Other factors relating to morphology and genetics are assessed to correlate sporozoite yield with a particular attribute(s). These factors include, but are not limited to, salivary gland size, length and size of the midgut, specific proteins and genetic markers. Such factors will be used in the progressive development of the strain of mosquito.

A composite scoring system preferably used to rank each female mosquito on her overall ability to sustain a high level of *Plasmodium* infection while satisfactorily completing those actions necessary to sustain a progressive mosquito and parasite life cycle. Those females with a high composite score will have their progeny retained for further cycles of this process. Selected progeny will be in-bred and cross-bred to steadily select for high-sporozoite infection tolerance.

Through continuous cycles, a highly refined, genetically distinct *Anopheles* strain capable of extremely high levels of *Plasmodium* infection and sporozoite production is created. Such an *Anopheles* strain preferably leads to more efficient production of viable whole cell sporozoites for use in an attenuated live or killed parasite vaccine.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

An additional aspect of the present invention includes an apparatus for injecting ultra-low volumes of vaccine suitable for attachment to standard syringes.

Figure 9A:
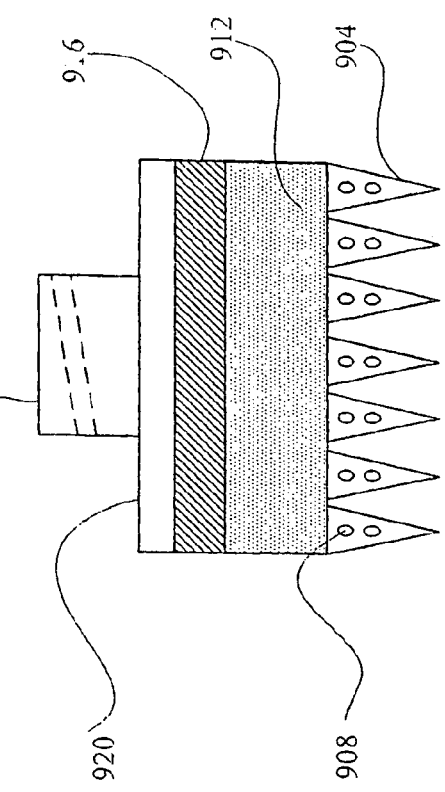
FIG. 9A is view of a micro-bolus vaccine assembly of the present invention.
Figure 9B:
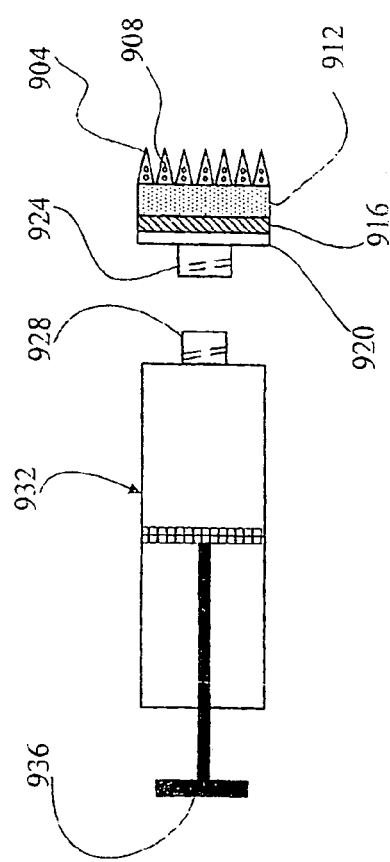
FIG. 9B is a view of a micro bolus vaccine assembly of the present invention.

An aspect of the present invention is an apparatus which will be referred to as a micro-bolus vaccine assembly (FIG. 9A 9B). The micro-bolus vaccine assembly preferably uses micro-needles 904 with multiple micro-pores 908. The micro-pores 908 deliver the total volume of the vaccine into hundreds or thousands of mini-boluses. The needles 904 are attached to a plastic reservoir 912 that holds a precise volume of the sporozoite vaccine. The necessary vaccine volume is calculated by multiplying the number of needles 904 by the desired volume of the mini-boluses plus the volume of the internal micro needles. Covering the reservoir 912 on the opposite side of the needles 904 is an elastic plate 916 that completely seals the reservoir 912. A plastic structure 920 with the same outside dimensions as the vaccine reservoir 912 is then attached. This plastic structure 920 has a standard female docking port 924 that attaches to the industry standard locking port of common syringes 928.

The micro-bolus vaccine assembly 900 is operated in the following manner. One to two milliliters of atmospheric gas is drawn into a syringe 932 and the micro-bolus vaccine assembly 900 is attached to the syringe 932. The needles 904 are placed into the patient's skin and the plunger 936 on the syringe is forcefully depressed. The gas inside the syringe 932 is compressed and travels into the micro-bolus vaccine assembly 900. The gas then deforms the elastic membrane 916. The membrane 916 pushes on the vaccine solution in the micro-bolus vaccine assembly reservoir 912. The vaccine is extruded in micro-boluses through the micro-pores 908 into the cutaneous tissues. The elastic membrane 916 prevents the gas in the syringe 932 from passing into the vaccine reservoir 912 of the micro-bolus vaccine assembly 900.

An additional aspect of the present invention is a method for the development of cyropreservation/freeze resistant *Plasmodium* species sporozoites.

A high temperature cryopreservable *Plasmodium* species may be developed by employing the following procedure. Heterogeneous strains or a homogenous strain of *Plasmodium* species gametocytes/ookinetes are mixed in a blood culture and fed to *Anopheles* mosquitoes. Ookinetes randomly assort and form zygotes within the midgut of the female mosquitoes.

The *Plasmodium* parasites are then allowed to develop into sporozoites, Seventy-two hours before the extraction of the sporozoites from the mosquitoes, the mosquitoes are subject to four to six hour intervals of slowly decreasing temperatures that plateau above their survival tolerance level and then are allowed to rise back to baseline temperatures. This activates cellular mechanisms that produce stabilizing proteins, enzymes, and sugar complexes that prime the sporozoites to withstand cyropreservation.

The sporozoites are then preferably extracted and purified from the whole body mosquito extract or salivary glands according to techniques that are well known among those of skill in the art.

Sporozoites are then preferably cryopreserved at temperatures from minus seventy degrees to zero degrees Celsius in ten to twenty degree increments in selected media suitable for direct immunization in humans. Portions of these sporozoites are thawed in vitro and assessed for motility and other markers of viability.

Sporozoites are then preferably thawed and injected into humans or animals. Once the human/animal becomes parasitemic, a blood sample is extracted and placed into a blood culture. The cycle of culturing, infection, and freezing is repeated several times.

Sporozoites that successfully survive cyropreservation and demonstrate the capacity to complete their full life cycle in both the mosquito and human or animal host will be sequentially selected and in-bred with themselves and back-bred to other successful strains to ultimately produce a highly infectious, high cyropreservation temperature tolerant strain of the *Plasmodium* parasite.

Sporozoite Attenuation and Preparation

Subsequently, a sub-chamber 901 with infected mosquitoes may be exposed to irradiation or other means described herein to attenuate the *Plasmodium* sporozoites in-vivo. Approximately 14 days after the mosquitoes have fed on the *Plasmodium* species infected blood meal, range 11-21 days, sub-chamber 901 is removed from the temperature and light controlled insectary and transported to a gamma or x-ray irradiator. An irradiator using a cobalt gamma source is preferable, but irradiators using a cesium gamma source or electron/cathode-ray tube x-ray emitter are acceptable. The mosquitoes within sub-chamber 901 are irradiated with a dose of radiation sufficient to deliver 15,000 Rads (+/−15%) within the interior of sub-chamber 901 at a rate of 1000 Rads per minute, range 150-30,000 Rads per minute. Following irradiation, the mosquitoes have received a dose of radiation that attenuates the sporozoites within their salivary glands and tissues. The sporozoites are now non-replicating, but still metabolically active. They are non-infectious to human or animal hosts, but still able to produce new proteins. Following irradiation, sub-chamber 901 is moved to a bio-hood for salivary gland extraction and sporozoite purification.

Mosquitoes are then collected by means of a suctioning tube or other such device inserted through neck 902, 909, or 904 after removal of cap 930, fine mesh screen 950 or cap 906 as necessary and desired. Though irradiating the infected mosquitoes prior to removal from sub-chamber 901 is not absolutely necessary, prior irradiation attenuates the parasites in-vivo and will ultimately kill the mosquitoes.

Following removal, aseptic irradiated infected mosquitoes are anesthetized by exposure to 4 degrees C. for 5 min or by exposure to chloroform or other anesthesizing substance. The mosquitoes are then transferred to a dissection dish containing medium 199 supplemented with a high molecular weight protein source, generally 10% human serum albumin. In some cases they may be dipped in 70% ethanol and washed in sterile insect physiological medium, medium 199 or water before being transferred for dissection. Individual mosquitoes are then immobilized with a needle on a glass slide in a small volume of this media. With the aid of a dissecting microscope, an instrument, generally a needle, is used to remove the mosquitoes' heads exposing the salivary glands. The tip of the instrument is then used to excise the salivary glands. Salivary glands are transferred with the tip of the instrument into a siliconized microfuge tube containing approximately 50 ul of supplemental media. Upon dissection of the required number of salivary glands, the volume of the siliconized microfuge tube is brought up to 500 ul with supplemental media. To release the sporozoites from the salivary glands, the suspension is manually aspirated back and forth 10-15 times with a 1 ml syringe attached to a fine gague needle 24 to 28 gague, preferably 26½ gauge. The sample is then vortexed at high speed. 10 ul of the suspension is loaded unto a double levy counting chamber (haemocytometer) for counting. At this time, the aseptic, attenuated sporozoites are ready for further processing for experimental protocols or vaccine production.

In the foregoing, the present invention has been described with reference to suitable embodiments, but these embodiments are only for purposes of understanding the invention and various alterations or modifications are possible so long as the present invention does not deviate from the claims that follow.

What is claimed is:

1. A method of producing aseptic sporozoite-stage *Plasmodium* parasites comprising:

a) providing a mosquito rearing chamber with solid walls and airtight seals, said walls enclosing a sterilized interior space and adapted for filtered air passage, said chamber separable into a first sub-chamber and a second sub-chamber adapted to receive a mosquito blood feeding station by which mosquitoes within said sub-chamber can feed;

b) aseptically transferring sterilized *Anopheles*-species eggs into said first sub-chamber and providing an aseptic larval rearing broth sufficient for the development of said eggs;

c) aseptically transferring said *Anopheles*-species to said second sub-chamber;

d) providing said blood feeding station with an aseptic blood meal, said blood meal comprising gametocyte-stage *Plasmodium* parasites such that said mosquitoes consume said blood meal and become infected with said *Plasmodium* parasites thereby; and, e) dissecting said mosquitoes to remove and pool sporozoite-containing salivary glands.

2. The method of claim 1, wherein said parasites are selected from the group consisting of *Plasmodium falciparum, Plasmodium vivax, Plasmodium ovale,* and *Plasmodium malariae.*

3. The method of claim 2 wherein said parasite is *Plasmodium falciparum.*

4. The method of claim 1 further comprising a treatment of *Plasmodium*-infected mosquitoes to attenuate parasites therein.

5. The method of claim 4 wherein the treatment is irradiation.

* * * * *